United States Patent
Watanabe et al.

(10) Patent No.: US 9,980,885 B2
(45) Date of Patent: May 29, 2018

(54) SILICONE-BASED COPOLYMER RESIN POWDER, MAKING METHOD, AND COSMETICS

(71) Applicant: Nissin Chemical Industry Co., Ltd., Echizen-shi, Fukui-ken (JP)

(72) Inventors: Kentaro Watanabe, Echizen (JP); Akira Yamamoto, Echizen (JP)

(73) Assignee: Nissin Chemical Industry Co. Ltd., Echizen-shi (JP)

( * ) Notice: Subject to any disclaimer, the term of this patent is extended or adjusted under 35 U.S.C. 154(b) by 0 days. days.

(21) Appl. No.: 14/529,247

(22) Filed: Oct. 31, 2014

(65) Prior Publication Data
US 2015/0125500 A1 May 7, 2015

(30) Foreign Application Priority Data

Nov. 1, 2013 (JP) .................. 2013-228283

(51) Int. Cl.
*A61K 8/02* (2006.01)
*A61Q 1/00* (2006.01)
*A61K 8/895* (2006.01)
*A61K 8/89* (2006.01)
*C08F 6/00* (2006.01)
*C08F 283/12* (2006.01)
*C08F 285/00* (2006.01)
*C08G 77/16* (2006.01)
*C08G 77/20* (2006.01)
*A61Q 1/02* (2006.01)
*A61Q 19/00* (2006.01)
*C08F 290/14* (2006.01)

(52) U.S. Cl.
CPC ............ *A61K 8/022* (2013.01); *A61K 8/0241* (2013.01); *A61K 8/0245* (2013.01); *A61K 8/89* (2013.01); *A61K 8/895* (2013.01); *A61Q 1/00* (2013.01); *A61Q 1/02* (2013.01); *A61Q 19/00* (2013.01); *C08F 6/008* (2013.01); *C08F 283/124* (2013.01); *C08F 285/00* (2013.01); *C08F 290/148* (2013.01); *C08G 77/16* (2013.01); *C08G 77/20* (2013.01); *A61K 2800/10* (2013.01); *A61K 2800/412* (2013.01); *A61K 2800/54* (2013.01); *A61K 2800/614* (2013.01); *A61K 2800/623* (2013.01); *A61K 2800/654* (2013.01)

(58) Field of Classification Search
CPC ........ A61K 8/022; A61K 8/89; A61K 8/0245; A61K 8/895; A61K 8/0241; C08F 6/008; C08F 283/124; C08F 285/00; C08F 290/148; C08G 77/16; C08G 77/20
See application file for complete search history.

(56) References Cited

U.S. PATENT DOCUMENTS

| 5,538,793 | A | 7/1996 | Inokuchi et al. | |
|---|---|---|---|---|
| 2004/0220302 | A1 | 11/2004 | Saegusa et al. | |
| 2008/0108751 | A1* | 5/2008 | Rogunova | ............... C08L 69/00 525/64 |
| 2012/0232220 | A1* | 9/2012 | Kimura | ................... C08J 3/226 525/63 |

FOREIGN PATENT DOCUMENTS

| JP | 3-162442 A | 7/1991 |
|---|---|---|
| JP | 4-342513 A | 11/1992 |
| JP | 5-78681 A | 3/1993 |
| JP | 7-33836 A | 2/1995 |
| JP | 7-196815 A | 8/1995 |
| JP | 11-228336 * | 8/1999 |
| JP | 2001-151626 A | 6/2001 |
| JP | 2002-3517 A | 1/2002 |
| JP | 2004-163513 A | 6/2004 |
| JP | 2010-83987 A | 4/2010 |
| WO | WO 2005/056624 A1 | 6/2005 |
| WO | WO 2009/128441 A1 | 10/2009 |
| WO | WO 2013/050149 A1 | 4/2013 |

OTHER PUBLICATIONS

Takeo et al., English Machine Translation of JP 11-228336, obtained on Feb. 3, 2016.*
Extended European Search Report, dated Mar. 18, 2015, for European Application No. 14190203.1.
Japanese Office Action, dated Dec. 19, 2017, for Japanese Application No. 2014-210960, with an English machine translation.

* cited by examiner

*Primary Examiner* — Johann R Richter
*Assistant Examiner* — Genevieve S Alley
(74) *Attorney, Agent, or Firm* — Birch, Stewart, Kolasch & Birch, LLP

(57) ABSTRACT

A silicone-based copolymer resin powder is prepared by reacting a siloxane oligomer obtained from ring-opening of (a1) a cyclic organosiloxane in the presence of (a3) an acid catalyst and (a4) an anionic surfactant with (a2) a silane coupling agent having an alkoxy group and a polymerizable double bond to obtain (A) a linear or branched organopolysiloxane containing at least 2 silicon-bonded hydroxyl groups per molecule,
copolymerizing (A) the linear or branched organopolysiloxane with (B) an ethylenically unsaturated monomer to form a copolymer as a core, and
further polymerizing to the copolymer another ethylenically unsaturated monomer as a shell,
the powder containing up to 0.3% by weight of the cyclic organosiloxane and up to 1% by weight of the anionic surfactant.

16 Claims, No Drawings

SILICONE-BASED COPOLYMER RESIN POWDER, MAKING METHOD, AND COSMETICS

CROSS-REFERENCE TO RELATED APPLICATION

This non-provisional application claims priority under 35 U.S.C. § 119(a) on Patent Application No. 2013-228283 filed in Japan on Nov. 1, 2013, the entire contents of which are hereby incorporated by reference.

TECHNICAL FIELD

This invention relates to a silicone-based copolymer resin powder which may be formulated in cosmetic compositions to impart slipperiness, soft tactility, and water repellency; a method for preparing the powder; and cosmetics comprising the powder.

BACKGROUND ART

From the past, silicone and acrylic-based synthetic resins in powder form are used in a variety of cosmetics such as hair care products, makeup cosmetics, and sunscreens since they form a uniform coating on the surface of skin or hair to keep the skin or hair moisturized and smooth or impart water repellency and water resistance.

For example, JP-A H07-196815 discloses silicone fine particles and JP-A 2001-151626 discloses acrylic resin fine particles. Since they are allegedly non-agglomerative and well dispersible and impart soft tactility, they are suitably formulated in cosmetics. Yet there exists a need for a powdered resin of better performance.

As is known in the art, an attempt is made to copolymerize a silicone component capable of imparting slipperiness and water repellency with an acrylic component capable of imparting compatibility, skin adhesion, and soft tactility. The resulting resin powder is useful in cosmetic application. For example, JP-A H03-162442 and JP-A H04-342513 disclose cosmetic compositions comprising a powdered resin obtained by graft polymerizing silicone to an acrylic backbone. There is still left room for improvement in slipperiness and tactility.

While resins obtained by graft polymerizing an acrylic component to a silicone backbone are also known, few find use in cosmetics. In the cosmetic application, silicone-acrylic copolymer resins based on silicone backbone are expected to be superior in slipperiness and tactility to those resins based on acrylic backbone. JP-A H05-078681 discloses a powdered resin based on a silicone component and having an acrylic component copolymerized therewith. This resin powder is used in industrial fields. However, it is not suited in cosmetic use for the following reason. It is synthesized by ring-opening polymerization of cyclic siloxane, which is equilibration reaction. Thus the emulsion after emulsion polymerization contains not only the polysiloxane, but also 5 to 10% by weight of residual cyclic siloxane. During storage or on use of the emulsion, the cyclic siloxane will volatilize off, adversely affecting physical stability and tactility. The amount of cyclic siloxane may be reduced by drying the emulsion into a powder, although the problem still remains unsolved. Therefore, it is desired to reduce the amount of residual cyclic siloxane in order that the emulsion may be used in the cosmetic application.

Under the circumstances, there is a desire to have a silicone-acrylic copolymer resin which is acceptable in the cosmetic application and has improved properties including extensibility, light feeling of quality, and soft tactility.

Citation List
Patent Document 1: JP-A H07-196815
Patent Document 2: JP-A 2001-151626
Patent Document 3: JP-A H03-162442
Patent Document 4: JP-A H04-342513
Patent Document 5: JP-A H05-078681

SUMMARY OF INVENTION

An object of the invention is to provide a silicone-acrylic copolymer resin powder which can be used in cosmetics to impart slipperiness and soft tacility; a method for preparing the powder; and cosmetics comprising the powder.

The inventors have succeeded in developing a silicone-acrylic copolymer resin powder which can be used in cosmetics.

In one aspect, the invention provides a silicone-based copolymer resin powder which is prepared by the steps of:

reacting a siloxane oligomer obtained from ring-opening of (a1) a cyclic organosiloxane in the presence of (a3) an acid catalyst and (a4) an anionic surfactant with (a2) a silane coupling agent having an alkoxy group and a polymerizable double bond to obtain (A) a linear or branched organopolysiloxane containing at least 2 silicon-bonded hydroxyl groups per molecule.

copolymerizing 100 parts by weight of (A) the linear or branched, organopolysiloxane with 1 to 899 parts by weight of (B) an ethylenically unsaturated monomer to form a copolymer as a core, and further polymerizing to the copolymer 1 to 899 parts by weight of another ethylenically unsaturated monomer as a shell, provided that the total amount of components (B) and (C) is 2 to 900 parts by weight, the powder containing up to 0.3% by weight of the cyclic organosiloxane and up to 1% by weight of the anionic surfactant, In a preferred embodiment, the siloxane oligomer has the general formula (1):

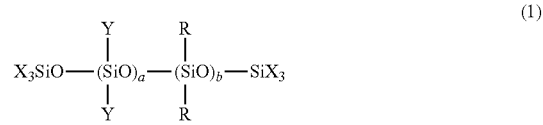

wherein R is each independently a substituted or unsubstituted $C_1$-$C_{20}$ alkyl or $C_6$-$C_{20}$ aryl group, X is each independently a substituted or unsubstituted $C_1$-$C_{20}$ alkyl, $C_6$-$C_{20}$ aryl, $C_1$-$C_{10}$ alkoxy, or hydroxyl group, Y is each independently a group: X or —[O—Si(X)$_2$]$_c$—X, at least two of X and Y are hydroxyl, a is a number of 0 to 1,000, b is a positive number of 100 to 10,000, and c is a positive number of 1 to 1,000.

In a preferred embodiment, the ethylenically unsaturated, monomer (B) is a (meth)acrylate, and the other ethylenically unsaturated monomer (C) comprises at least one methacrylate having the formula (3):

wherein $R^3$ is an alkyl group of at least 3 carbon atoms.

In another aspect, the invention provides a cosmetic composition comprising the silicone-based copolymer resin powder defined above.

In a further aspect, the invention provides a method for preparing a silicone-based copolymer resin powder, comprising the steps of:

reacting in water a siloxane oligomer obtained from ring-opening of (a1) a cyclic organosiloxane in the presence of (a3) an acid catalyst and (a4) an anionic surfactant with (a2) a silane coupling agent having an alkoxy group and a polymerizable double bond to obtain an emulsion of (A) a linear or branched organopolysiloxane containing at least 2 silicon-bonded hydroxyl groups per molecule, copolymerizing 100 parts by weight of (A) the linear or branched organopolysiloxane with 1 to 899 parts by weight of (B) an ethylenically unsaturated monomer to form a copolymer as a core, and further polymerizing to the copolymer 1 to 899 parts by weight of another ethylenically unsaturated monomer as a shell, for thereby yielding a silicone-based copolymer resin emulsion, provided that the total amount of components (B) and (C) is 2 to 900 parts by weight, drying the silicone-based copolymer resin emulsion, washing with an organic solvent, and drying again into powder form to obtain the silicone-based copolymer resin powder containing up to 0.3% by weight of the cyclic organosiloxane and up to 1% by weight of the anionic surfactant.

In a preferred embodiment, the ring-opening and polymerization step includes emulsifying and dispersing the cyclic organosiloxane (a1) and the silane coupling agent (a2) in water using the anionic surfactant (a4), adding the acid catalyst (a3) thereto, and effecting polymerization reaction for thereby forming the linear or branched organopolysiloxane.

In a preferred embodiment, the ring-opening and polymerization step is at a temperature of 55 to 85° C., more preferably 65 to 75° C.

In a preferred embodiment, 0.01 to 20 parts by weight of the silane coupling agent (a2) is used, 0.01 to 10 parts by weight of the acid catalyst (a3) is used, and 0.1 to 20 parts by weight of the anionic surfactant (a4) is used, each per 100 parts by weight of the cyclic organosiloxane (a1).

In a preferred embodiment, the ethylenically unsaturated monomer (B) is a (meth)acrylate, and the other ethylenically unsaturated monomer (C) comprises at least one methacrylate having an ester portion (COOR portion) of at least 4 carbon atoms.

In a preferred embodiment, the washing step uses at least one organic solvent selected from alcohol solvents and hydrocarbon solvents.

Advantageous Effects of Invention

The silicone-based copolymer resin powder is formulated in cosmetics such as hair care products, makeup cosmetics, and sunscreens to impart slipperiness, soft tactility, and water repellency.

DESCRIPTION OF EMBODIMENTS

As used herein, the terminology "($C_x$-$C_y$)", as applied to a particular unit, such as, for example, a chemical compound or a chemical substituent group, means having a carbon atom content of from "x" carbon atoms to "y" cartoon atoms per such unit. The terminology "(meth)acrylate monomers" refers collectively to acrylate monomers and methacrylate monomers.

One embodiment of the invention is a silicone-based copolymer resin powder, which is prepared by the steps of reacting in water a siloxane oligomer obtained from ring-opening of (a1) a cyclic organosiloxane in the presence of (a3) an acid catalyst and (a4) an anionic surfactant with (a2) a silane coupling agent having an alkoxy group and a polymerizable double bond to obtain an emulsion of (A) a linear or branched organopolysiloxane containing at least 2 silicon-bonded hydroxyl groups per molecule.

copolymerizing 100 parts by weight of (A) the linear or branched organopolysiloxane with 1 to 899 parts by weight of (B) an ethylenically unsaturated monomer to form a copolymer as a core, and further polymerizing to the copolymer 1 to 899 parts by weight of another ethylenically unsaturated monomer as a shell, for thereby yielding a silicone-based copolymer resin emulsion, provided that the total amount of components (B) and (C) is 2 to 900 parts by weight, drying the silicone-based copolymer resin emulsion, washing with an organic solvent to remove the surfactant remaining on particles, and drying again.

Component (A) is a linear or branched organopolysiloxane which is obtained from ring-opening and polymerization of components (a1), (a2), (a3) and (a4). In this case, the above siloxane oligomer obtained from ring-opening of the cyclic organosiloxane should contain at least 2 silicon-bonded hydroxyl groups per molecule and preferably have the general formula (1).

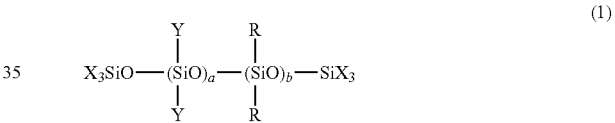

Herein R is each independently a substituted or unsubstituted $C_1$-$C_{20}$ alkyl or $C_6$-$C_{20}$ aryl group, X is each independently a substituted or unsubstituted $C_1$-$C_{20}$ alkyl, $C_6$-$C_{20}$ aryl, $C_1$-$C_{20}$ alkoxy, or hydroxyl group, Y is each independently a group: X or —[O—Si(X)$_a$]$_c$—X, at least two of X and Y are hydroxyl, a is a number of 0 to 1,000, b is a positive number of 100 to 10,000, and c is a positive number of 1 to 1,000.

Specifically, R which may be the same or different is selected from substituted or unsubstituted $C_1$-$C_{20}$ alkyl groups and $C_6$-$C_{20}$ aryl groups, for example, methyl, ethyl, propyl, butyl, pentyl, hexyl, heptyl, octyl, nonyl, decyl, dodecyl, tetradecyl, hexadecyl, octadecyl, cyclopentyl, cyolohexyl, cycloheptyl, phenyl, tolyl, and naphthyl, with methyl being preferred. Substituted alkyl groups include the foregoing alkyl groups substituted with a halogen atom, acryloxy, methacryloxy, carboxy, alkoxy, alkenyloxy, amino, alkyl, or alkoxy- or (meth)acryloxy-substituted amino radical.

X which may be the same or different is selected from substituted or unsubstituted $C_1$-$C_{20}$ alkyl groups, $C_6$-$C_{20}$ aryl groups, $C_1$-$C_{20}$ alkoxy groups and hydroxyl groups. Exemplary groups (excluding hydroxyl) include methyl, ethyl, propyl, butyl, pentyl, hexyl, heptyl, octyl, nonyl, decyl, dodecyl, tetradecyl, hexadecyl, octadecyl, cyclopentyl, cyolohexyl, cycloheptyl, phenyl, tolyl, naphthyl, methoxy, ethoxy, propoxy, butoxy, hexyloxy, heptyloxy, octyloxy, decyloxy, and tetradecyloxy. Substituted alkyl groups are as exemplified above.

Y which may be the same or different is X or —[O—Si(X)$_2$]$_c$—X. At least two of X and Y groups are hydroxyl. That is, from the standpoint of crosslinking, the compound should contain at least 2 hydroxyl groups, preferably 2 to 4 hydroxyl groups per molecule, specifically at both ends.

The subscript "a" is a number of 0 to 1,000, preferably 0 to 200. The subscript "b" is a positive number of 100 to 10,000, preferably 1,000 to 5,000. If b is smaller than 100, film flexibility may become poor. If b is greater than 10,000, film tear strength may become low. The subscript "c" is a positive number of 1 to 1000, preferably 1 to 200.

Illustrative examples of the organopolysiloxane are shown below.

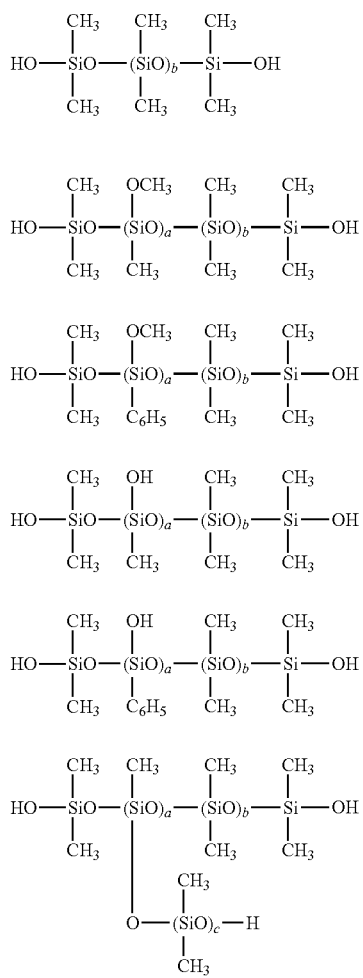

Herein a, b and c are as defined above.

As alluded to above, the siloxane oligomer is obtained from ring-opening of (a1) a cyclic organosiloxane, typically octamethylcyelotatrasiloxane in the presence of (a3) an acid catalyst. Since siloxane oligomer is typically used, in emulsion form, it may be prepared as emulsion by any well-known emulsion polymerization methods. In this context, the siloxane oligomer may be readily obtained by previously emulsifying and dispersing the cyclic organosiloxane (a1) and the silane coupling agent (a2) in water using an anionic surfactant (a4), adding the acid catalyst (a3) thereto, and effecting polymerization reaction.

Examples of the cyclic organosiloxane (a1) include hexamethylcyclotrisiloxane (B3), octamethylcyclotetrasiloxane (D4), decamethylcyclopentasiloxane (D5), dodecamethylcyclohexasiloxane (D6), 1,1-diethylhexamethylcyclotetrasiloxane, phenylheptamthylcyclotetrasiloxane, 1,1-diphenylhexamethylcyclotetrasiloxane, 1,3,5,7-tetravinyltetramethylcyclotetrasiloxane, 1,3,5,7-tetramethyloyclotetrasiloxane, 1,3,5,7-tetracyolohexyltetramethylcyclotetrasiloxane, tris(3,3,3-trifluoropropyl)trimethylcyclotrisiloxane, 1,3,5,7-tetra(3-methacryloxypropyl)tetramethylcyclotetrasiloxane,
1,3,5,7-tetra(3-acryloxypropyl)tetramethylcyclotetrasiloxane,
1,3,5,7-tetra(3-carboxypropyl)tetramethylcyclotetrasiloxane,
1,3,5,7-tetra(3-vinyloxypropyl)tetramethylcyclotetrasiloxane,
1,3,5,7-tetra(p-vinylphenyl)tetramethylcyolotetrasiloxane,
1,3,5,7-tetra[3-(p-vinylphenyl)propyl]tetramethylcyclotetrasiloxane,
1,3,5,7-tetra(N-acryloyl-N-methyl-3-aminopropyl)tetramethyl-cyclotetrasiloxane,
1,3,5,7-tetra(N,N-bis(lauroyl)-3-aminopropyl)tetramethyl-cyclotetrasiloxane.

When a siloxane is expressed by the number of cyclic dimethyl units (D unit of the molecular formula: SiO(CH$_3$)$_2$) bonded, siloxanes D3 to D20 are included. Preferred are cyclic siloxanes of [SiO(CH$_3$)$_2$]$_n$ wherein n is an integer of 3 to 10. More preferred are octamethylcyclotetrasiloxane and decamethylcyclopentasiloxane.

In the present invention, the siloxane oligomer obtained by the ring-opening is reacted with a silane coupling agent (a2) having an alkoxy group and a polymerizable double bond.

The silane coupling agent (a2) is an organosilicon compound containing an alkoxy group and a polymerizable double bond. The polymerizable double bond is vinyl group, allyl group, acryloxy group, methacryloxy group, and the like. It typically has the general formula (2):

$$R^1_{(4-d-e)}R^0_e Si(OR^2)_2 \quad (2)$$

wherein R$^1$ is a monovalent organic group having a polymerizable double bond, typically an acryloxy or methacryloxy-substituted C$_1$-C$_6$ alkyl group, R$^0$ is C$_1$-C$_4$ alkyl, R$^2$ is C$_1$-C$_4$ alkyl, d is an integer of 1 to 3, e is an integer of 0 to 2, and e+d=1 to 3. Preferably, d is 2 or 3, e is 0 or 1, and e+d=2 or 3.

Examples of the silane coupling agent include vinylsilanes such as vinyltrixnethoxysilane, vinyltriethoxysilane, vinyltripropoxysilane, vinyltriisopropoxysilane, vinylmethyldimethoxysilane, and vinylmethyldiethoxysilane; and acrylsilanes such as γ-(meth)acryloxypropyltrimethoxysilane, γ-(meth)acryloxypropyltriethoxysilane, γ-(meth)acryloxypropyltripropoxysilane, γ-(meth)acryloxypropyltriisopropoxysilane, γ-(meth)acryloxypropyltributoxysilane, γ-(meth)acryloxypropylmethyldimethoxysilane, γ-(meth)acryloxypropylmethyldiethoxysilane, γ-(meth)acryloxypropylmethyldipropoxysilane, γ-(meth)acryloxypropylmethyldiisopropoxysilane, and γ-(meth)acryloxypropylmethyldibutoxysilane. Of these, ethoxy-bearing silanes are most desirable when the alcohol generated therefrom is taken into account.

The silane coupling agent (a2) is preferably used in an amount of 0.01 to 20 parts, more preferably 0.01 to 5 parts by weight per 100 parts by weight of the cyclic organosiloxane (a1).

In the practice of the invention, the cyclic organopolysiloxane (a1) and the silane coupling agent (a2) are emulsified and dispersed in water by using the anionic surfactant (a4), followed by adding the acid catalyst (a3) thereto, and effecting polymerization reaction for thereby the linear or branched arganopolysiloxane having at least 2 hydroxyl groups bonded to silicon atoms and a polymerizable double bond in a molecule.

For example, when octamethylcyclotetrasiloxane as the cyclic organosiloxane and γ-methacryloxypropylmethyl-dimethoxysilane as the silane coupling agent are used, the reaction proceeds as follows.

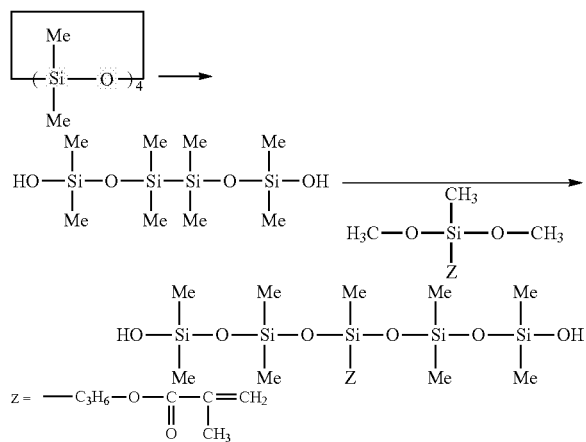

In the above reaction, the acid catalyst (a3) may be selected from those catalysts commonly used in polymerization reactions. Examples include dodecylbenzenesulfonic acid, hydrochloric acid, sulfuric acid, phosphoric acid, citric acid, lactic acid, and ascorbic acid. Inter alia, dodecylbenzenesulfonic acid is preferred because the salts it forms after neutralization are not restricted by the Pharmaceutical Affairs Law, Cosmetics Standards, are described in the Standards of Quasi-drug Ingredients 2006, fall outside the poisonous and deleterious substances defined in the Poisonous and Deleterious Substances Control Law, and are not restricted by the Pollutant Release and Transfer Restster (PRTR) Law in Japan. Also preferred are phosphoric acid, citric acid, lactic acid, and ascorbic acid which themselves are not subject to such legal restrictions.

The acid catalyst (a3) is preferably used in an amount of 0.01 to 10 parts, more preferably 0.2 to 2 parts by weight per 100 parts by weight of the cyclic organosiloxane (a1). Outside the range, smaller amounts of the acid catalyst may lead to short reaction. If the amount of the acid catalyst is too large, a more amount of alkali must be added for neutralization and as a result, the emulsion may become unstable due to a reduced solids content and an increased amount of metal ions.

The anionic surfactant (a4) may be selected from those surfactants commonly used in polymerization reactions. Preferred are least-irritating surfactants which are not restricted by the Pharmaceutical Affairs Law, Cosmetics Standards, are described in the Standards of Quasi-drug Ingredients 2006, fall outside the poisonous and deleterious substances defined in the Poisonous and Deleterious Substances Control Law, and are not restricted by the Pollutant Release and Transfer Resister (PRTR) Law in Japan. Suitable anionic surfactants include H-acylamino acid salts, N-acyltaurine salts, fatty acid soaps, and alkylphosphates, and those surfactants which are readily soluble in water and free of ethylene oxide chain are more preferred. Specifically, N-acylamino acid salts having a $C_1$-$C_{20}$ acyl moiety, N-acyltaurine salts having a $C_{10}$-$C_{20}$ acyl moiety, $C_{10}$-$C_{20}$ fatty acid soaps, and $C_{10}$-$C_{20}$ alkylphosphates are preferred. The preferred salts are alkali metal salts. Most preferred are sodium cocoil methyl taurate, sodium lauroyl methyl taurate and sodium myristoyl methyl taurate.

The anionic surfactant (a4) is preferably used in an amount of 0.1 to 20 parts, more preferably 0.5 to 10 parts by weight per 100 parts by weight of the cyclic organosiloxane (a1). Outside the range, smaller amounts of the surfactant may fail in emulsification or form an extremely unstable emulsion whereas larger amounts may cause short reaction of the cyclic organosiloxane.

In combination with the anionic surfactant, a nonionic surfactant such as polyoxyethylene alkyl ether may be used. However, the nonionic surfactant, when used alone, fails to exert surface activity because polymerization takes place under high temperature, acidic conditions.

During emulsion polymerization of the reactants, water is preferably used in an amount of 50 to 200 parts by weight per 100 parts by weight of the cyclic organosiloxane (a1).

For the polymerization, any well-known methods and conditions may be employed. The polymerization reaction has a tendency that a degree of polymerization increases at a higher temperature when the catalyst is a weak acid. The polymerization temperature is preferably 55 to 85° C., more preferably 65 to 75° C. If the polymerization temperature is as low as room temperature, ring opening of the cyclic siloxane may not occur or occur insufficiently. At higher temperature beyond the range, the emulsion may not remain stable. Although the polymerization time may be determined as appropriate, the preferred time is about 1 to 40 hours.

As a result of polymerization reaction, the linear or branched organopolysiloxane having at least 2 silicon-bonded hydroxyl groups and a polymerizable double bond in molecule (A) is obtained in emulsion form. The emulsion may be used as such, or after it is diluted with water or concentrated to a solids content of 20 to 50% by weight, preferably 30 to 50% by weight, as the case may be.

Then, (B) an ethylenically unsaturated monomer is graft polymerized to the organopolysiloxane (A) to form a core.

Suitable ethylenically unsaturated monomers of component (B) to be grafted include ethylene, propylene; conjugated diene monomers such as 1,3-butadiene and 2-methyl-1,3-butadiene; ethylenically unsaturated monocarboxylic acid esters such as methyl acrylate, ethyl acrylate, butyl acrylate, 2-ethylhexyl acrylate, and methyl methacrylate; ethylenically unsaturated dicarboxylic acid esters such as dimethyl itaconate, diethyl maleate, monobutyl maleate, monoethyl fumarate, and dibutyl fumarate; ethylenically unsaturated monocarboxylic acids such as acrylic acid, methacrylic acid, and crotonic acid; ethylenically unsaturated dicarboxylic acids such as itaconic acid, maleic acid and fumaric acid; epoxy-containing monomers such as glycidyl methacrylate; alcoholic hydroxyl-containing monomers such as 2-hydroxyethyl methacrylate; alkoxy-containing monomers such as methoxyethyl acrylate; nitril-containing monomers such as acrylonitrile; amide-containing monomers such as acrylamide; amino-containing monomers such as dimethylaminoethyl methacrylate; and monomers having at least 2 ethylenically unsaturated groups per molecule such as divinylbenzene and allyl methacrylate.

Of these, (meth)acrylates are preferred, for example, methyl acrylate, ethyl acrylate, n-butyl acrylate, lauryl acrylate, methyl methacrylate, ethyl methacrylate, and n-butyl methacrylate.

During graft polymerization, the ethylenically unsaturated monomer (B) is used in an amount of 1 to 899 parts, preferably 40 to 400 parts by weight per 100 parts by weight of the organopolysiloxane (A). A polymer containing less than 1 part of monomer (B) may be difficult to be powdered whereas a polymer containing more than 899 parts of monomer (B) may lose tactility.

For graft polymerization, the temperature is typically 50 to 95° C., preferably 60 to 85° C., and the time is typically 1 to 40 hours, preferably 4 to 10 hours. The graft polymerization is preferably carried out in an inert gas atmosphere such as nitrogen gas.

Further, another ethylenically unsaturated monomer of component (C) is used to form a shell. Component (C) is the same as or different from component (B), although components (B) and (C) are preferably different each other. Preferably the monomer (C) comprises at least one methacrylate having the formula (3):

$$H_2C=CH(CH_3)COOR^3 \qquad (3)$$

wherein $R^3$ is an alkyl group of at least 3 carbon atoms, preferably 3 to 12 carbon atoms, and more preferably 3 to 6 carbon atoms.

Suitable methacrylates include methyl methacrylate, ethyl methacrylate, propyl methacrylate. butyl methacrylate, hexyl methacrylate, cyclohexyl methacrylate, octyl methacrylate, decyl methacrylate, dodecyl methacrylate, tetradecyl methacrylate, lauryl methacrylate, benzyl methacrylate, and phenyl methacrylate. Preferably the monomer (C) comprises at least one alkyl methacrylate of formula (3) having an alkyl group of at least 3 carbon atoms (excluding methyl methacrylate and ethyl methacrylate). Specifically the monomer (C) comprises at least one of isopropyl methacrylate, isobutyl methacrylate, t-butyl methacrylate, sec-butyl methacrylate, cyclohexyl methacrylate, benzyl methacrylate, phenyl methacrylate, and 2-hydroxyethyl methacrylate.

It is preferred for reactivity with the silicone portion that the ethylenically unsaturated monomer (C) comprise 10 to 100% by weight, especially 30 to 100% by weight of the methacrylate of formula (3). Besides the methacrylate of formula (3), the monomer (C) may contain a monomer which is preferably an acrylate.

Preferably the ethylenically unsaturated monomer (C) is such that a homopolymer may have a glass transition temperature (Tg) of at least 40° C., more preferably at least 60° C. The upper limit of Tg is preferably up to 200° C., more preferably up to 150° C. It is noted that Tg is measured according to JIS K7121.

The ethylenically unsaturated monomer (C) is used in an amount of 1 to 899 parts, preferably 40 to 400 parts by weight per 100 parts by weight of the organopolysiloxane (A). Less than 1 part of monomer (C) may be ineffective for forming a shell and invite agglomeration whereas a polymer containing more than 899 parts of monomer (C) may lose tactility.

In this case, the total amount of components (B) and (C) is 2 to 900 parts by weight, preferably 80 to 800 parts by weight per 100 parts by weight of component (A).

The polymerization may be continued by post-adding the ethylenically unsaturated monomer of component (C) in the silicone-based graft copolymer resin emulsion.

For shell-forming polymerization, the temperature is typically 50 to 95° C., preferably 60 to 85° C., and the time is typically 1 to 40 hours, preferably 4 to 10 hours. The polymerization is preferably carried out in an inert gas atmosphere such as nitrogen gas.

The silicone-based copolymer resin emulsion thus obtained preferably has a solids content of about 20 to 50% by weight, more preferably about 30 to 50% by weight. Also preferably, the emulsion has a viscosity at 25° C. of 10 to 5,000 mPa·s, especially 50 to 1,000 mPa·s, as measured by a Brookfield viscometer. Further preferably, the emulsion has an average particle size of up to 1 μm, especially 100 to 300 nm, as measured by a particle size distribution analyzer of laser diffraction, and scattering method. Further preferably, the emulsion is at pH 6 to 8.

The silicone-based copolymer resin emulsion is then concentrated by suitable means such as thermal dehydration, filtration, centrifugation or decantation, and optionally washed with water, and dried by suitable wafer removal means such as heat drying under atmospheric or reduced pressure, spray drying (of spraying the dispersion into gas stream), or heat drying via flowing heat medium. The drying temperature is preferably 60 to 105° C. In this way, there are obtained powder particles. If agglomerates are present, the powder may be disintegrated by a suitable disintegrator such as a jet mill, ball mill or hammer mill.

Since some cyclic organosiloxane and surfactant remain in the resin powder, the powder is preferably washed with an organic solvent to remove such residues. The preferred organic solvents include alcohol and hydrocarbon solvents, specifically lower alcohols of 1 to 4 carbon atoms and aliphatic hydrocarbons of 5 to 20 carbon atoms. For example, methanol, ethanol, isopropyl alcohol, hexane and isododecane are preferably used. The washing procedure is, for example, by feeding 100 parts by weight of the powder into a beaker, adding at least 500 parts by weight (at least 5 times the weight of the powder) of the organic solvent thereto, agitating for several hours, and suction filtering. Better results are obtained when this is followed by washing with the same solvent or with water if the solvent used for washing is a water-soluble solvent like alcohol. The washing procedure is typically carried out at room temperature although an elevated temperature is acceptable.

The washing is followed by drying again, obtaining a powder. The powder collected by filtration is typically dried on a dryer at a temperature of 40 to 200° C. for several hours, or a flow dryer may be used. The resin powder thus obtained preferably has an average particle size of up to 15 μm, more preferably 0.1 to 10 μm.

Notably, some cyclic organosiloxane and surfactant remain in the silicone-based copolymer resin emulsion. Desirably, the amounts of residual cyclic organosiloxane and surfactant are reduced by 100 to 90% from the charged amounts, respectively. Further desirably, the content of residual cyclic organosiloxane in the final silicone-based copolymer resin powder is up to 0.3% by weight, more desirably up to 0.1% by weight, and the content of residual surfactant is up to 1% by weight, more desirably up to 0.5% by weight.

The silicone-based copolymer resin powder may find use in cosmetics. A further embodiment of the invention is a cosmetic composition comprising the silicone-based copolymer resin powder. Typically the resin powder is formulated in an amount of 2 to 50% by weight of the cosmetic composition. Less than 2 wt % of the resin powder may fail to exert the desired effect whereas more than 50 wt % may be unfavorable as cosmetics, for example, appearing outstandingly white.

Besides the silicone-based copolymer resin powder, other ingredients such as oil, solvent, and powder (other than the silicone-based copolymer resin powder) may be formulated in the cosmetic composition. Suitable oils include hydrocarbons, silicone oils, triglyceride, ester oils, oils and fats, waxes, higher fatty acids of 12 to 20 carbon atoms, and higher alcohols of 8 to 20 carbon atoms. Inter alia, low-boiling silicone oils, low-boiling isoparaffin hydrocarbons, triglyceride, and ester oils are preferred. Exemplary of the low-boiling silicone oils are octamethylayelotetrasiloxane, decamethylcyclopentasiloxane, and tetradecamethylcyclohexasiloxane. Exemplary of the ester oils are fatty acid esters of 6 to 20 carbon atoms and glycerol fatty acid esters.

In the cosmetic composition, the amount of oil varies with the form of cosmetic composition and may be determined appropriate as long as the effects of the invention are not impaired. Preferably the oil is contained in an amount of 0.1 to 95%, more preferably 1 to 80% by weight based on the total weight of the inventive resin powder and other powder. Less than 0.1 wt % of the oil may fail to exert its slippery and humectant effects whereas more than 95 wt % of the oil tends to adversely affect storage stability.

Suitable solvents include medium to lower alcohols and aromatic alcohols. Lower alcohols of 1 to 4 carbon atoms such as isopropyl alcohol are preferred. In the cosmetic composition, the amount of solvent varies with the form of cosmetic composition and may be determined appropriate as long as the effects of the invention are not impaired. Preferably the solvent is contained in an amount of 0.1 to 80%, more preferably 1 to 50% by weight based on the total weight of the inventive resin powder and other powder.

The material of the other powder is not particularly limited as long as materials are acceptable for use in (makeup) cosmetic compositions. Typically the powder has an average particle size of 0.1 to 50 μm. For example, colorants such as inorganic coloring pigments, inorganic white pigments, and organic pigments, pearly agents, extender pigments, and organic powders are useful.

Suitable inorganic powder materials include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, lithia mica, silicic acid, silicic anhydride, aluminum silicate, sodium silicate, sodium magnesium silicate, magnesium silicate, aluminum magnesium silicate, calcium silicate, barium silicate, strontium silicate, metal tungstates, hydroxyapatite, vermiculite, Higilite®, bentonite, montmorillonite, hectorite, zeolite, ceramic powder, calcium secondary phosphate, alumina, aluminum hydroxide, and boron nitride. Suitable organic powder materials include polyamide powder, polyester powder, polyethylene powder, polypropylene powder, polystyrene powder, polyurethane powder, benzoguanamine powder, polymethylbenzoguanamine powder, polytetrafluoroethylene powder, polymethyl methacrylate powder, cellulose, silk powder, nylon powder, 12-nylon, 6-nylon, silicone powder, polymethylsilsesquioxane spherical powder, styrene-acrylic acid copolymers, divinylbenzene-styrene copolymers, vinyl resins, urea resins, phenolic resins, fluoro-resins, silicon resins, acrylic resins, melamine resins, epoxy resins, polycarbonate resins, microcrystalline fibril powder, starch powder, and lauroyl lysine. Suitable surfactant metal salt powders include zinc stearate, aluminum stearate, calcium stearate, magnesium stearate, zinc myristate, magnesium myristate, zinc palmitate, zinc laurate, zinc cetylphosphate, calcium cetylphosphate, and zinc sodium cetylphosphate. Suitable color pigments include inorganic red pigments such as red iron oxide, iron oxide, iron hydroxide, iron titanate, inorganic brown pigments such as γ-iron oxide, inorganic yellow pigments such as yellow iron oxide and ochre, inorganic black pigments such as black iron oxide and carbon black, inorganic purple pigments such as manganese violet and cobalt violet, inorganic green pigments such as chromium hydroxide, chromium oxide, cobalt oxide, and cobalt titanate, inorganic blue pigments such as Prussian blue and ultramarine; lake-form tar pigments such as Red #3, Red #104, Red #106, Red #201, Red #202, Red #204, Red #205, Red #220, Red #226, Red #227, Red #228, Red #230, Red #401, Red #505, Yellow #4, Yellow #5, Yellow #202, Yellow #203, Yellow #204, Yellow #401, Blue #1, Blue #2, Blue #201, Blue #404, Green #3, Green #201, Green #204, Green #205, Orange #201, Orange #203, Orange #204, Orange #206, Orange #207, etc.; lake-form natural dyes such as carminic acid, laccaic acid, carthamia, brazilin and crocin. Suitable pearly pigments include titania-coated mica, titanated mica, iron oxide-treated titanated mica, bismuth oxychloride, titania-coated bismuth oxychloride, titania-coated talc, fish scales, and titania-coated colored mica. Suitable metal powder pigments include aluminum, gold, silver, copper, platinum and stainless steel in powder form.

Besides the foregoing ingredients, any other ingredients may be formulated in the cosmetic composition of the invention as long as the amount and nature of the ingredient are limited so as not to compromise the effects of the silicone-based copolymer resin powder of the invention. Suitable other ingredients include surfactants, oily ingredients, polymers, gelling agents, alkaline agents, polyhydric alcohols, pH modifiers, UV absorbers, antioxidants, preservatives, anti-inflammatory agents, skin conditioning agents, perfumes and others commonly used in cosmetics.

Examples of the cosmetic composition include makeup cosmetics such as foundations, face powders, eye shadow, eyeliner, eyebrow colors, cheek colors, lip colors, nail colors; basic cosmetics or skin care products such as milky lotion, cream, lotion, calamine lotion, sunscreen, suntan lotion, after shave lotion, pre-shave lotion, pack, acne treatment, and essence; hair care cosmetics such as shampoo, rinse, conditioner, hair color, hair tonic, setting agent, hair nutrient, permanent wave agent; body powder, deodorant, depilatory, soap, body shampoo, bath preparation, hand soap, and perfume. The cosmetic composition comprising the silicone-based copolymer resin powder is best suited as powdered cosmetics such as foundations, face powders, eye shadow, and eyebrow colors.

EXAMPLE

Preparation Examples, Examples, and Comparative Examples are given below by way of illustration and not by way of limitation. All parts and % are by weight.

Preparation Example 1

A 2-L polyethylene beaker was charged with 499.6 g of octamethylcyclotetrasiloxane, 0.4 g of γ-methacryloxypropylmethyldiethoxysilane, 5 g of sodium lauryl sulfate in 45 g of deionized water, and 5 g of dodecylbenzenesulfonic acid in 45 g of deionized water. Using a homomixer, the contents were uniformly emulsified. The emulsion was diluted by gradually adding water in a total amount of 400 g, and passed twice through a high-pressure homogenizer under a pressure of 300 kgf/cm$^2$, yielding a uniform white emulsion. The emulsion was transferred to a 2-L glass flask equipped with a stirrer, thermometer and reflux condenser, where polymerization reaction was run at 55° C. for 24 hours. The emulsion was aged at 10° C. for 24 hours and neutralized to pH 6.2 with 12 g of 10% sodium carbonate aqueous solution. The emulsion had a nonvolatile content of 45.4% when dried at 105° C. for 3 hours, and the organopolysiloxane in the emulsion was a non-flowing soft gel. While 214 g of methyl methacrylate (MMA) was added dropwise to the emulsion over 3-5 hours, redox reaction was carried out at 40° C. using peroxide and reducing agent, for thereby effecting acrylic graft polymerization to silicone. Similarly, while 143 g of methyl methacrylate and 143 g of cyclohexyl methacrylate were added dropwise to the emulsion over 3-5 hours, shell-forming polymerization was carried out, obtaining a resin emulsion.

The emulsion was adjusted to a concentration of 10-30% and spray dried at 100° C. into a resin powder.

Methanol, 200 g, was added to 20 g of the powder, followed by stirring for about 1 hour. After decantation, the powder was washed with 200 g of methanol again. Wet powder was collected by suction filtration and dried at 105° C. for 1 hour until the volatile content decreased below 1%, obtaining a desired silicone-based copolymer resin powder (Preparation Example 1).

The contents of residual cyclic organosiloxane and surfactant were quantitatively determined by GC and HPLC, respectively.

Preparation Examples 2 to 8 and Comparative Preparation Examples 1 to 7

As in Preparation Example 1, silicone-based copolymer resin powders were prepared according to the formulation in Tables 1 and 2.

TABLE 1

| Component/Amount (pbw) | | Preparation Example | | | | | | | |
|---|---|---|---|---|---|---|---|---|---|
| | | 1 | 2 | 3 | 4 | 5 | 6 | 7 | 8 |
| a1 | D4 | 97.9 | 97.9 | 93.4 | 93.4 | 93.4 | 93.5 | 93.4 | 90.8 |
| a2 | KBE-502 | 0.1 | 0.1 | 0.1 | 0.1 | 0.1 | 0.1 | 0.1 | 0.1 |
| a3 | LAA | 1.0 | 1.0 | | | | | | |
| | Phosphoric acid | | | 2.8 | 2.8 | 2.8 | | 2.8 | 3.9 |
| | Citric acid | | | | | | 1.0 | | |
| a4 | SLS | 1.0 | 1.0 | | | | | | |
| | LMT | | | 3.7 | 3.7 | 3.7 | 5.4 | 3.7 | 5.2 |
| | (A) | 100 | 100 | 100 | 100 | 100 | 100 | 100 | 100 |
| (B) | MMA | 42 | 42 | 28 | 28 | 28 | | 28 | 39 |
| | BA | | | | | | 40 | | |
| (C) | MMA | 28 | 88 | 28 | 93 | | 40 | | 52 |
| | CHMA | 28 | 98 | 9 | | 37 | 13 | | |
| | i-BMA | | | | | | | 37 | |
| | Tg (° C.) of component (C) polymer | 72 | 70 | 88 | 105 | 44 | 88 | 67 | 105 |
| | (B) + (C) | 170 | 298 | 153 | 121 | 65 | 181 | 65 | 91 |
| | Washing | yes | yes | yes | yes | yes | yes | yes | yes |
| | Particle size (μm) | 7 | 8 | 7 | 8 | 8 | 9 | 8 | 8 |
| | Cootent of residual D4 (ppm) | 210 | 180 | 250 | 150 | 300 | 100 | 210 | 210 |
| | Content of residual surfactant (ppm) | 210 | 230 | 300 | 250 | 220 | 320 | 310 | 310 |

TABLE 2

| Component/Amount (pbw) | | Comparative preparation Example | | | | | | |
|---|---|---|---|---|---|---|---|---|
| | | 1* | 2 | 3 | 4 | 5 | 6 | 7 |
| a1 | D4 | | 97.9 | 97.9 | 97.1 | 95.5 | 97.9 | 97.9 |
| a2 | KBE-502 | | 0.1 | 0.1 | 0.1 | 0.1 | 0.1 | 0.1 |
| a3 | LAA | 1.0 | 1.0 | 1.0 | 1.4 | 2.2 | 1.0 | 1.0 |
| | Phosphoric acid | | | | | | | |
| | Citric acid | | | | | | | |
| a4 | SLS | 1.0 | 1.0 | 1.0 | 1.4 | 2.2 | 1.0 | 1.0 |
| | LMT | | | | | | | |
| | (A) | | 100 | 100 | 100 | 100 | 100 | |
| (B) | MMA | 100 | | 42 | 97 | 223 | 42 | 42 |
| | BA | | | | | | | |
| (C) | MMA | | | | | | | 56 |
| | CHMA | | | | | | | |
| | i-BMA | | | | | | | |
| | (B) + (C) | | | 42 | 97 | 223 | 42 | 98 |
| | Washing | no | no | no | no | no | yes | no |
| | Particle size (μm) | 23 | power available | 25 | 20 | 19 | 32 | 15 |
| | Content of residual D4 (ppm) | 0 | | 5,000 | 3,000 | 1,500 | 300 | 4,800 |
| | Content of residual surfactant (ppm) | 18,500 | | 20,000 | 20,000 | 19,000 | 280 | 20,000 |

*In Comparative Preparation Example 1, MMA was polymerized with LAA and SLS.

D4: octamethyltetrasiloxane
KBE-502: γ-methacryloxypropylmethyldiethoxysilane
LAA: dodecylbensenesulfonic acid
SLS: sodium lauryl sulfate
LMT: sodium lauroyl methyl taurate
MMA: methyl methacrylate
BA: butyl acrylate
CHMA: cyclohexyl methacrylate
i-BMA: isobutyl methacrylate Example 1

Using the resin powder of Preparation Example 1, a foundation was prepared according to the following formulation.

| Ingredients | Amount (%) |
| --- | --- |
| (1) Silicone-based copolymer resin powder of Preparation Example 1 | 3.0 |
| (2) Acrylic-silicone-treated talc[1] | balance |
| (3) Acrylic-silicone-treated sericite | 10.0 |
| (4) Metal soap-treated mica | 2.0 |
| (5) Synthetic phlogopite | 5.0 |
| (6) Spherical silica powder | 5.0 |
| (7) Silicone-treated microparticulate titania | 12.5 |
| (8) Silicone-treated red iron oxide | 0.6 |
| (9) Silicone-treated yellow iron oxide | 2.0 |
| (10) Silicone-treated black iron oxide | 0.2 |
| (11) Silicone-treated titania | 6.0 |
| (12) Diisostearyl malate | 2.0 |
| (13) Glyceryl triisostearate | 0.4 |
| (14) Methylpolysiloxane | 3.5 |
| (15) UV absorber | 5.0 |
| (16) Preservative | appropriate |
| (17) Perfume | appropriate |

Note:
[1] NS Talc JA-46R-3F (Kakuhachi Co., Ltd.)

Examples 2 to 8 and Comparative Examples 1 to 7

Foundations were prepared according to the same formulation as in Example 1.

Example 9

A foundation was prepared according to the same formulation as in Example 1 except that 20% of the resin powder of Preparation Example 1 was used.

These foundations were evaluated by the following tests, with the results shown in Tables 3 and 4.

Tactility and Slipperiness

A panel of 20 members conducted an application test to evaluate the tactility and slipperiness of cosmetic. A sample was given a point by each member according to the following criterion and rated by the total of points.

| Point | Remarks |
| --- | --- |
| 5 | excellent |
| 4 | good |
| 3 | ordinary |
| 2 | poor |
| 1 | very poor |

| Rating | Total point (TP) |
| --- | --- |
| ◉ | TP ≥ 80 |
| ○ | 60 ≤ TP < 80 |
| Δ | 40 ≤ TP < 60 |
| X | TP < 40 |

Oil Absorption

Using a spatula on aluminum foil, small amounts of jojoba oil were sequentially added and mixed with about 2 g of powder so that the powder might absorb oil. The oil feed was stopped when the powder/oil mixture became pasty so that the spatula might be smoothly moved around. The amount of oil fed (absorbed) is expressed in ml/100 g. The amount of oil absorbed is preferably at least 120 ml, more preferably at least 130 ml.

TABLE 3

| | Example | | | | | | | | |
| --- | --- | --- | --- | --- | --- | --- | --- | --- | --- |
| | 1 | 2 | 3 | 4 | 5 | 6 | 7 | 8 | 9 |
| Powder | Preparation Example | | | | | | | | |
| used | 1 | 2 | 3 | 4 | 5 | 6 | 7 | 8 | 1 |
| Amount | 3.0% | 3.0% | 3.0% | 3.0% | 3.0% | 3.0% | 3.0% | 3.0% | 20% |
| Tactility | ◉ | ◉ | ◉ | ◉ | ◉ | ◉ | ◉ | ◉ | ◉ |
| Amount of oil absorbed (ml) | 145 | 155 | 135 | 145 | 150 | 135 | 150 | 125 | 145 |
| Slipperiness | ◉ | ◉ | ◉ | ◉ | ◉ | ◉ | ◉ | ○ | ◉ |

TABLE 4

| | Comparative Example | | | | | | |
| --- | --- | --- | --- | --- | --- | --- | --- |
| | 1 | 2 | 3 | 4 | 5 | 6 | 7 |
| | Comparative Preparation Example | | | | | | |
| Powder used | 1 | 2 | 3 | 4 | 5 | 6 | 7 |
| Amount | 3.0% | — | 3.0% | 3.0% | 3.0% | 3.0% | 3.0% |
| Tactility | ○ | — | X | X | X | ○ | ○ |
| Amount of oil absorbed (ml) | 80 | — | 100 | 110 | 90 | 110 | 95 |
| Slipperiness | ○ | — | X | X | X | ○ | X |

As is evident from the test results, the silicone-acrylic copolymer resin powder of the invention is drastically improved in tactility and oil absorption over conventional acrylic powder, silicone rubber powder and the acrylic-silicone resin by the prior art method.

Japanese Patent Application No. 2013-228283 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:
1. A silicone-based copolymer resin powder which is prepared by the steps of:
reacting a siloxane oligomer obtained from ring-opening of (a1) a cyclic organosiloxane in the presence of (a3) an acid catalyst and (a4) an anionic surfactant with (a2)

a silane coupling agent having an alkoxy group and a polymerizable double bond to obtain (A) a linear or branched organopolysiloxane containing at least 2 silicon-bonded hydroxyl groups per molecule, graft copolymerizing 100 parts by weight of (A) the linear or branched organopolysiloxane with 1 to 899 parts by weight of (B) an ethylenically unsaturated monomer to form a silicone-based graft copolymer resin emulsion as a core, wherein (B) has one ethylenically unsaturated group per monomer, and further polymerizing to the copolymer 1 to 899 parts by weight of (C), which is an ethylenically unsaturated monomer comprising at least one monomer different from (B), as a shell, provided that the total amount of components (B) and (C) is 2 to 900 parts by weight, wherein the silicone-based copolymer resin powder contains up to 0.3% by weight of the cyclic organosiloxane and up to 1% by weight of the anionic surfactant, and wherein the silicone-based copolymer resin powder does not include a cross-linking agent.

2. The silicone-based copolymer resin powder of claim 1 wherein the siloxane oligomer has the general formula (1):

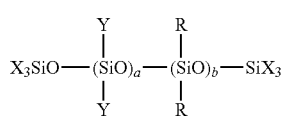

wherein R is each independently a substituted or unsubstituted $C_1$-$C_{20}$ alkyl or $C_6$-$C_{20}$ aryl group, X is each independently a substituted or unsubstituted $C_1$-$C_{20}$ alkyl, $C_6$-$C_{20}$ aryl, $C_1$-$C_{20}$ alkoxy, or hydroxyl group, Y is each independently a group: X or —[O—Si(X)$_2$]$_c$—X, at least two of X and Y are hydroxyl, a is a number of 0 to 1,000, b is a positive number of 100 to 10,000, and c is a positive number of 1 to 1,000.

3. The silicone-based copolymer resin powder of claim 1 wherein the ethylenically unsaturated monomer (B) is a (meth)acrylate, and the other ethylenically unsaturated monomer (C) comprises at least one methacrylate having the formula (3):

$$H_2C=CH(CH_3)COOR^3 \quad (3)$$

wherein $R^3$ is an alkyl group of at least 3 carbon atoms.

4. The silicone-based copolymer resin powder of claim 1, further comprising a step of washing the silicone-based graft copolymer after further polymerizing to the copolymer 1 to 899 parts by weight of (C).

5. A cosmetic composition comprising a silicone-based copolymer resin powder, said powder is prepared by the steps of:

reacting a siloxane oligomer obtained from ring-opening of (a1) a cyclic organosiloxane in the presence of (a3) an acid catalyst and (a4) an anionic surfactant with (a2) a silane coupling agent having an alkoxy group and a polymerizable double bond to obtain (A) a linear or branched organopolysiloxane containing at least 2 silicon-bonded hydroxyl groups per molecule, graft copolymerizing 100 parts by weight of (A) the linear or branched organopolysiloxane with 1 to 899 parts by weight of (B) an ethylenically unsaturated monomer to form a silicone-based graft copolymer resin emulsion as a core, wherein (B) has one ethylenically unsaturated group per monomer, and further polymerizing to the copolymer 1 to 899 parts by weight of (C), which is an ethylenically unsaturated monomer comprising at least one monomer different from (B), as a shell, provided that the total amount of components (B) and (C) is 2 to 900 parts by weight, wherein the silicone-based copolymer resin powder contains up to 0.3% by weight of the cyclic organosiloxane and up to 1% by weight of the anionic surfactant, and wherein the silicone-based copolymer resin powder does not include a cross-linking agent.

6. A silicone-based copolymer resin powder which is prepared by the steps of:

reacting a siloxane oligomer obtained from ring-opening of (a1) a cyclic organosiloxane in the presence of (a3) an acid catalyst and (a4) an anionic surfactant with (a2) a silane coupling agent having an alkoxy group and a polymerizable double bond to obtain (A) a linear or branched organopolysiloxane containing at least 2 silicon-bonded hydroxyl groups per molecule;

graft copolymerizing 100 parts by weight of (A) the linear or branched organopolysiloxane with 1 to 899 parts by weight of (B) an ethylenically unsaturated monomer to form a silicone-based graft copolymer resin emulsion as a core, wherein (B) has one ethylenically unsaturated group per monomer; and further polymerizing to the copolymer 1 to 899 parts by weight of (C), which is an ethylenically unsaturated monomer with at least one monomer different from (B), as a shell, provided that the total amount of components (B) and (C) is 2 to 900 parts by weight, wherein the silicone-based copolymer resin core consists of components (A) and (B), and wherein the silicone-based copolymer resin powder contains up to 0.3% by weight of the cyclic organosiloxane and up to 1% by weight of the anionic surfactant.

7. The silicone-based copolymer resin powder of claim 6, wherein the silicone-based copolymer resin consists of components (A), (B) and (C).

8. A method for preparing a silicone-based copolymer resin powder, comprising the steps of:

reacting in water a siloxane oligomer obtained from ring-opening of (a1) a cyclic organosiloxane in the presence of (a3) an acid catalyst and (a4) an anionic surfactant with (a2) a silane coupling agent having an alkoxy group and a polymerizable double bond to obtain an emulsion of (A) a linear or branched organopolysiloxane containing at least 2 silicon-bonded hydroxyl groups per molecule, graft copolymerizing 100 parts by weight of (A) the linear or branched organopolysiloxane with 1 to 899 parts by weight of (B) an ethylenically unsaturated monomer to form a silicone-based graft copolymer resin emulsion as a core, wherein (B) has one ethylenically unsaturated group per molecule, further polymerizing to the copolymer 1 to 899 parts by weight of (C), which is an ethylenically unsaturated monomer comprising at least one monomer different from (B), as a shell, for thereby yielding a silicone-based copolymer resin emulsion, provided that the total amount of components (B) and (C) is 2 to 900 parts by weight, drying the silicone-based copolymer resin emulsion, washing with an organic solvent, and drying again into powder form to obtain the silicone-based copolymer resin powder containing up to 0.3% by weight of the cyclic organosiloxane, up to 1% by weight of the anionic surfactant and does not include a cross-linking agent.

9. The method of claim 8 wherein the ring-opening and polymerization step includes emulsifying and dispersing the cyclic organosiloxane (a1) and the silane coupling agent (a2) in water using the anionic surfactant (a4), adding the acid catalyst (a3) thereto, and effecting polymerization reaction for thereby forming the linear or branched organopolysiloxane.

10. The method of claim 8, wherein the ring-opening and polymerization step is at a temperature of 55 to 85° C.

11. The method of claim 10 wherein the ring-opening polymerization step is at a temperature of 65 to 75° C.

12. The method of claim 8 wherein 0.01 to 20 parts by weight of the silane coupling agent (a2) is used per 100 parts by weight of the cyclic organosiloxane (a1).

13. The method of claim 8 wherein 0.01 to 10 parts by weight of the acid catalyst (a3) is used per 100 parts by weight of the cyclic organosiloxane (a1).

14. The method of claim 8 wherein 0.1 to 20 parts by weight of the anionic surfactant (a4) is used per 100 parts by weight of the cyclic organosiloxane (a1).

15. The method of claim 8 wherein the ethylenically unsaturated monomer (B) is a (meth)acrylate, and the other ethylenically unsaturated monomer (C) A comprises at least one methacrylate having an ester portion of at least 4 carbon atoms.

16. The method of claim 8 wherein the washing step uses at least one organic solvent selected from alcohol solvents and hydrocarbon solvents.

* * * * *